(12) United States Patent
Huang et al.

(10) Patent No.: US 10,201,641 B2
(45) Date of Patent: Feb. 12, 2019

(54) SUSTAINED RELEASE INTRAOCULAR IMPLANTS AND METHODS FOR TREATING OCULAR VASCULOPATHIES

(71) Applicant: Allergan, Inc., Irvine, CA (US)

(72) Inventors: Glenn T. Huang, Fremont, CA (US); Brittany Jackson, Fort Worth, TX (US); James A. Burke, Santa Ana, CA (US); Ton Lin, Mission Viejo, CA (US); Patrick M. Hughes, Aliso Viejo, CA (US); Larry A. Wheeler, Irvine, CA (US); Rosy Sheng Donn, Saratoga, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/886,376

(22) Filed: Oct. 19, 2015

(65) Prior Publication Data
US 2016/0038654 A1    Feb. 11, 2016

Related U.S. Application Data

(60) Continuation of application No. 12/024,010, filed on Jan. 31, 2008, now Pat. No. 9,161,938, which is a division of application No. 10/836,911, filed on Apr. 30, 2004, now abandoned.

(51) Int. Cl.
| | | |
|---|---|---|
| *A61L 31/14* | (2006.01) | |
| *A61K 31/498* | (2006.01) | |
| *C08L 67/04* | (2006.01) | |
| *A61K 9/20* | (2006.01) | |
| *A61L 31/16* | (2006.01) | |
| *A61L 27/58* | (2006.01) | |
| *A61K 9/00* | (2006.01) | |
| *A61K 47/34* | (2017.01) | |
| *A61L 31/06* | (2006.01) | |

(52) U.S. Cl.
CPC .......... *A61L 31/148* (2013.01); *A61K 9/0051* (2013.01); *A61K 9/204* (2013.01); *A61K 31/498* (2013.01); *A61K 47/34* (2013.01); *A61L 27/58* (2013.01); *A61L 31/06* (2013.01); *A61L 31/16* (2013.01); *C08L 67/04* (2013.01); *A61L 2300/436* (2013.01); *A61L 2300/604* (2013.01); *Y02A 50/401* (2018.01)

(58) Field of Classification Search
CPC .............................. A61K 9/0051; A61L 31/16
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,396,625 A | 8/1983 | Yamamori et al. |
| 4,425,346 A | 1/1984 | Horlington et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |

(Continued)

FOREIGN PATENT DOCUMENTS

| | | |
|---|---|---|
| CA | 1333770 | 1/1995 |
| CA | 2294714 | 1/1999 |

(Continued)

OTHER PUBLICATIONS

Acheampong, Andrew, Distribution of Brimonidine Into Anterior and Posterior Tissues of Monkey, Rabbit, and Rat Eyes, The American Society for Pharmacology and Experimental Therapeutics, Jan. 4, 2002, 421-429, 30 (4), US.

(Continued)

*Primary Examiner* — Kyle A Purdy
(74) *Attorney, Agent, or Firm* — Laura L. Wine

(57) ABSTRACT

Biocompatible intraocular implants include an alpha-2 adrenergic receptor agonist and a polymer associated with the alpha-2 adrenergic receptor agonist to facilitate release of the alpha-2 adrenergic receptor agonist into an eye for an extended period of time. The alpha-2 adrenergic receptor agonist may be associated with a biodegradable polymer matrix, such as a matrix of a two biodegradable polymers. The implants may be placed in an eye to treat one or more ocular conditions, such as an ocular vasculopathy or glaucoma, among others.

6 Claims, 7 Drawing Sheets

(56) References Cited

U.S. PATENT DOCUMENTS

| | | |
|---|---|---|
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,501,856 A | 3/1996 | Ohtori et al. |
| 5,504,074 A | 4/1996 | D'Amato et al. |
| 5,587,371 A | 12/1996 | Sessler et al. |
| 5,587,479 A | 12/1996 | Makovec et al. |
| 5,597,897 A | 1/1997 | Ron et al. |
| 5,632,984 A | 5/1997 | Wong et al. |
| 5,655,832 A | 8/1997 | Pelka et al. |
| 5,656,297 A | 8/1997 | Berstein et al. |
| 5,688,819 A | 11/1997 | Woodward et al. |
| 5,707,643 A | 1/1998 | Ogura |
| 5,766,242 A | 6/1998 | Wong et al. |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch |
| 5,856,329 A | 1/1999 | Wheeler |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,051,576 A | 4/2000 | Ashton et al. |
| 6,066,675 A | 5/2000 | Wen et al. |
| 6,074,661 A | 6/2000 | Olejnik et al. |
| 6,194,415 B1 | 2/2001 | Wheeler |
| 6,217,869 B1 | 4/2001 | Meyer et al. |
| 6,217,895 B1 | 4/2001 | Guo et al. |
| 6,225,303 B1 | 5/2001 | Miller et al. |
| 6,248,741 B1 | 6/2001 | Wheeler |
| 6,258,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,297,240 B1 | 10/2001 | Embleton |
| 6,306,426 B1 | 10/2001 | Olejnik et al. |
| 6,309,669 B1 | 10/2001 | Setterstrom et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,403,649 B1 | 6/2002 | Woodward |
| 6,410,045 B1 | 6/2002 | Schultz |
| 6,447,796 B1 | 9/2002 | Vook et al. |
| 6,455,062 B1 | 9/2002 | Olejnik et al. |
| 6,465,464 B2 | 10/2002 | Wheeler et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,573,280 B2 | 6/2003 | Dreyer |
| 6,595,945 B2 | 7/2003 | Brown |
| 6,692,759 B1 | 2/2004 | Wong et al. |
| 6,699,493 B2 | 3/2004 | Wong |
| 6,713,081 B2 | 3/2004 | Robinson et al. |
| 6,726,918 B1 | 4/2004 | Wong et al. |
| 6,765,012 B2 | 7/2004 | Andrews et al. |
| 7,091,232 B2 | 8/2006 | Chow |
| 7,368,126 B2 | 5/2008 | Chen et al. |
| 7,589,057 B2 | 9/2009 | Chang et al. |
| 8,293,210 B2 | 10/2012 | Huang et al. |
| 8,293,741 B2 | 10/2012 | Burke et al. |
| 8,506,986 B2 | 8/2013 | Huang et al. |
| 2001/0023363 A1 | 9/2001 | Harth et al. |
| 2001/0049369 A1 | 12/2001 | Jablonski |
| 2002/0032201 A1 | 3/2002 | Olejnik |
| 2002/0040015 A1 | 4/2002 | Miller et al. |
| 2002/0094998 A1 | 7/2002 | Burke et al. |
| 2002/0111357 A1 | 8/2002 | Wheeler et al. |
| 2003/0018078 A1 | 1/2003 | Woodward et al. |
| 2003/0069286 A1 | 4/2003 | Chen et al. |
| 2003/0069560 A1 | 4/2003 | Adamis et al. |
| 2003/0095995 A1 | 5/2003 | Wong et al. |
| 2003/0157178 A1 | 8/2003 | Chen et al. |
| 2003/0185873 A1 | 10/2003 | Chasin et al. |
| 2003/0199478 A1 | 10/2003 | Andrews et al. |
| 2003/0225152 A1 | 12/2003 | Andrews et al. |
| 2004/0013704 A1 | 1/2004 | Kabra et al. |
| 2004/0054374 A1 | 3/2004 | Weber et al. |
| 2004/0151753 A1 | 8/2004 | Chen et al. |
| 2004/0208910 A1 | 10/2004 | Ashton et al. |
| 2004/0266776 A1 | 12/2004 | Gil |
| 2005/0059664 A1 | 3/2005 | Gil et al. |
| 2005/0154399 A1 | 7/2005 | Weber et al. |
| 2005/0244506 A1 | 10/2005 | Burke et al. |
| 2005/0244458 A1 | 11/2005 | Huang et al. |
| 2005/0244463 A1 | 11/2005 | Huang |
| 2005/0244476 A1 | 11/2005 | Burke et al. |
| 2005/0244479 A1 | 11/2005 | Huang et al. |
| 2006/0233860 A1 | 10/2006 | Chang |
| 2008/0112922 A1 | 5/2008 | Hughes et al. |
| 2008/0118547 A1 | 5/2008 | Jackson et al. |
| 2008/0118548 A1 | 5/2008 | Jackson et al. |
| 2008/0118549 A1 | 5/2008 | Huang et al. |
| 2008/0131372 A1 | 6/2008 | Huang et al. |
| 2008/0131485 A1 | 6/2008 | Huang et al. |
| 2008/0260832 A1 | 10/2008 | Huang et al. |
| 2008/0299178 A1 | 12/2008 | Huang et al. |
| 2011/0251201 A1 | 10/2011 | Huang et al. |

FOREIGN PATENT DOCUMENTS

| | | |
|---|---|---|
| EP | 0364417 | 4/1990 |
| EP | 0488401 | 6/1992 |
| EP | 0430539 | 10/1994 |
| EP | 0992244 | 4/2000 |
| WO | 1995-013765 | 5/1995 |
| WO | 1996-038174 | 12/1996 |
| WO | 2001-030323 | 5/2001 |
| WO | 2001-058240 | 8/2001 |
| WO | 2001-070230 | 9/2001 |
| WO | 2002-002076 | 1/2002 |

(56) References Cited

FOREIGN PATENT DOCUMENTS

| WO | 2002-036162 | 5/2002 |
|---|---|---|
| WO | 2002-043785 | 6/2002 |
| WO | 2003-077952 | 9/2003 |
| WO | 2003-099795 | 12/2003 |
| WO | 2004-066979 | 8/2004 |
| WO | 2005-110367 | 11/2005 |
| WO | 2005-110368 | 11/2005 |

OTHER PUBLICATIONS

Allergan, Alphagan Product Information, Product Sheet, 2005, 1-10.
Allergan, Inc., Tazorac Product Information Sheet, 2004, 1-8.
AlphaganP, Physician's Desk Reference, Product Information, 54th Edition, 493-494, 2001.
Anderson, Lynne et al, An Injectable Sustained Release Fertility Control System, Contraception, 1976, 375-384, 13.
Baker, Richard, Controlled Release of Biologically Active Agent, A Wiley, 1987, 73-75, Interscience Publication.
Bartlett, J.D. et al, Contrast Sensitivity Improvements in Brimonidine-Treated Primary Open-Angle Glaucoma Patients Suggest a Neuroprotective Mechanism, ARVO Meeting, 2002, 1 Page, Biosis.
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts and New Perspectives, Archives of Ophthalmology, 1987, 1036-1039, 105.
Bito, LZ, Prostaglandins, Other Eicosanoids, and Their derivatives as Potential Antiglaucoma Agents, Glaucoma: Applied Pharmacology, 1984, 477-505, 20.
Bodor, Nicholas et al, A Comparison of Intraocular Pressure Elevating Activity of Loteprednoletabonate and Dexamethasone in Rabbits, Current Eye Research, 1992, 525-530, 11.
Brubaker, Richard, Mechanism of Action of Bimatoprost (LumiganTM), Surv Ophthalmol, 2001, S347-S351, 45-Suppl 4.
Busse, Dagmar et al, Tyrosine Kinase Inhibitors: Rationale, Mechanisms of Action, and Implications for Drug Resistance, Semin Oncol, 2001, 47-55, 28-Suppl 16.
CAS Registry Record from STN-59803-98-4, 1984, 1 Page.
Charles, Jean-Bernard et al, Use of Bioerodible Polymers Impregnated with Mitomycin in Glaucoma Filtration Surgery in Rabbits, Ophthalmology, Apr. 1991, 503-508, 98-4.
Chen, June et al, LumiganR: A Novel Drug for Glaucoma Therapy, Optom In Pract., Jun. 12, 2002, 95-102, 3.
Cheng, Cheng-Kuo et al., Intravitreal Sustained-Release Dexamethasone Device in the Treatment of Experimental Uveites, Investigative Ophthalmology & Visual Science, 1995, 442-453, 96 (2), US.
Chiang, Chiao-Hsi et al, Pharmacokinetics and Intraocular Pressure Lowering Effect of Timolol Preparations in Rabbit Eyes, Journal of Ocular Pharmacology and Therapeutics, 1996, 471-480, 12(4).
Cleland, Jeffrey et al, Development of Poly-(D,L-lactide-coglycolide) Microsphere Formulations Containing Recombinant Human Vascular Endothelial Growth Factor to Promote Local Angiogenesis, Journal of Controlled Release, 2001, 13-24, 72.
Clive, Migdal, Lumigan(R): A New Ocular Hypotensive Agent for Achieving Target Intraocular Pressure, Acta Ophthalmol Scand Scientific Abstracts, 2002, 457, 80-4.
Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.
Conti, B. et al., Biodegradable Microspheres for the Intravitreal Administration of Acyclovir In Vitro/In Vivo Evaluation, European Journal of Pharmaceutical Sciences, 1997, 287-293, 5.
Coquelet, P. et al, Successful Photodynamic Therapy Combined with Laser Photocoagulatio in Three Eyes With Classic Subfoveal Choroidal Neovascularisation Affecting Two Patients With Multifocal Choroiditis: Case Reports, Bull. Soc. Beige Ophthalmal, 2002, 69-73, 283.

De Jong, S.J. et al, New insights into the hydrolytic degradation of poly(lactic acid): participation of the alcohol terminus, Polymer, 2001, 2795-2802, 42.
Di Colo, Giacomo, Controlled Drug Release From Implantable Matrices Based on Hydrophobic Polymers, Biomaterials, 1992, 850-856, 13(12).
Enyedi, Laura et al, An Intravitreal Device Providing Sustained Release of Cyclosporins and Dexamethason, Current Eye Research, 1996, 549-557.
Epstein, David, Primary Open-Angle Glaucoma, Chandler and Grants Glaucoma, 1986, 129-181.
Evans, D.W. et al, Contrast Sensitivity Improves After Brimonidine Therapy in Primary Open Angle Glaucoma: A Case for Neuroprotection, Br. J. Ophthalmol, 2003, 1463-1465, 87.
Fabbro, Doriano et al, Protein Tyrosine Kinase Inhibitors: New Treatment Modalities?, Current Opinion in Pharmacology, 2002, 374-381, 2.
Fotsis, Theodore et al, The Endogenous Oestrogen Metabolite 2-methoxyoestradiol inhibits Angiogeneses and Suppresses Tumour Growth, Current Opinion in Pharmacology, 1994, 368, 237.
Furrer, Pascal et al, Ocular Tolerance of Preservatives and Alternatives, European Journal of Pharmaceutics and Biopharmaceutics, 2002, 263-280, 53.
Gao, Hua et al, Up-Regulation of Brain-Derived Neurotrophic Factor Expressior by Brimonidine in Rat Retinal Ganglion Cells, Arch. Ophthalmol., 2002, 797-803, 120.
Goel, Sanjay et al, Tyrosine Kinase Inhibitors: A Clinical Perspective, Current Oncology Reports, 2002, 9-19, 4.
Guenther, Lyn, Optimizing Treatment with Topical Tazarotene, Am. J. Clin. Dermotol, 2003, 197-202, 4-3.
Hainsworth, Dean et al, Sustained Release Intravitreal Dexamethasone, Journal of Ocular Pharmacology and Therapeutics, 1996, 57-63, 12-1.
Haluska, Paul et al, Receptor tyrosine kinase inhibitors, Current Opinion in Investigational Drugs, 2001, 280-286, 2-2.
Hare, William et al, Efficacy and Safety of Memantine, an NMDA-Type Open-Channel Blocker, from Reduction of Retinal Injury associated with Experimental Glaucoma in Rat and Monkey, Sur Ophthalmol, 2001, S284-S289, 45-Suppl. 3.
Hashizoe, Mototane et al, Scleral Plugof Biodegradable Polymers for Controlled Drug Release in the Vitreous, Arch Ophthalmol, 1994, 1380-1384, 112.
Haynes, Robert Jr, Adrenocorticotropic Hormone; Adrenocortical Steroids and Their Synthetic Analogs; Inhibitors of the Synthesis and Actions of Adrenocotical Hormones, The Pharmacological Basis of Therapeutics, 1990, 1431-1462, 8th Edition.
Heller, J., Hydrogels in Medicine and Pharmacy, N.A. Peppes ed., 1987, 137-149.
Heller, Jorge, Biodegradable Polymers in Controlled Drug Delivery, Critical Reviews in Therapeutic Drug Carrier Systems, 1987, 39-90, 1 (1).
Hoyng, Philip et al, Pharmacological Therapy for Glaucoma, Drugs 2000, 2000, 411-434, 59 (3), US.
Hubbard, Stevan et al, Protein Tyrosine Kinase Structure and Function, Annu. Rev. Biochem., 2000, 373-98, 69.
Jackanicz, Theodore et al, Polyactic Acid as a Biodegradable Carrier for Contraceptive Steroids, Contraception, 1973, 227-235, 8-3.
Jampel, Henry et al, Glaucoma Filtration Surgery in Monkeys Using 5-Fluorouridine in Polyanhydride Disks, Arch Ophthalmol, Mar. 1990, 430-435, 108.
John Wiley, Encyclopedia of polymer science and Engineering, 1985, vol. 3.
Kimura, Hideya et al, A New Vitreal Drug Delivery System Using an Implantable Biodegradable Polymeric Device, Invest Ophthalmol Vis Sci, 1994, 2815-2819, 35.
Kochinke, F. et al, Biodegradable Drug Delivery System for Uveitis Treatment, Investigative Ophthalmology & Visual Science, Feb. 15, 1996, 186-B98, 37(3).
Kwak, Hyung Woo et al, Evaluation of the Retinal Toxicity and Pharmacokinetics of Dexamethasone After Intravitreal Injection, Arch. Ophthalmol, 1992, 259-66, 110.

(56) References Cited

OTHER PUBLICATIONS

Lai, Ronald et al, Alpha-2 Adrenoceptor Agonist Protects Retinal Function After Acute Retinal Ischemic Injury in the Rat, Vis Neurosci, 2002, 175-185, 19.
Lee, David et al, Glaucoma Filtration Surgery in Rabbits Using Bioerodible Polymers and 5-Fluorouacil, Ophthalmol, Dec. 1987, 1523-1530, 94-12.
Lee, David et al, The Use of Bioerodible Polymers and 5-Fluorouracils in Glaucoma Filtration Surgery, Ophthalmology & Visual Science, Nov. 1988, 1692-1697, 29-11.
Lee, Susan et al, Biodegradable Implants for Sustained Drug Release in the Eye, Pharm Res, 2010, 2043-2053, 27.
Lewis, Danny, Controlled Release of Bioactive Agents from Lactide/Glycolide Polymers, Biodegradable Polymers as Drug Delivery Systems, 1990, 1-35, 45.
Macular Degeneration Genetics, Oct. 31, 2006, http://macular-degeneration.emedtv.com/macular-degeneration/macular-degeneration-genetics.html, 1 Page.
Marks, R., Topical Tazarotene:Review and Re-Evaluation, Retinoids, 2001, 72-74, 17(3).
Maurice, David, Micropharmaceutics of the Eye, Ocular Inflammation Ther., 1983, 97-102, 1.
Mayo Clinic Com, Stargardt's Disease: Can It Be Treated?, May 27, 2008, 2 Pages.
Merck Manuals, Retinitis Pigmentosa, 2005, http://merck.com/mmpe/print/sec09/ch106/ch106h.html, printed May 27, 2008. 2 Pages.
Merkli, Alain et al, Use of Insoluble Biodegradable Polymers in Ophthalmic Systems for the Sustained Release of Drugs, European Journal of Pharmaceutics and Biopharmaceutics, 1995, 271-283, 41 (5), US.
Miller, Robert et al, Degradation Rates of Oral Resorbable Implants (Polyactates and Polyglycolates): Rate Modification with Changes in PLA/PGA Copolymer Ratios, J. Biomed Materials Res, 1977, 711-719, 11.
Miller, Thomas et al, Synthesis and Structure-Activity Profiles of A-Homoestranes, the Estratopones, J. Med. Chem., 1997, 3836-3841, 40.
Moshfeghi, Darius et al, Retinal and Choroidal Vascular Occlusion After Posterior Sub-Tenon Triamcinolone Injection, American Journal of Ophthalmology, 2002, 132-134, vol. 134.
Mundorf, Thomas, et al., Evaluation of the Comfort of Alphagan P Compared with Alphagan in Irritated Eyes, Advances in Therapy, Nov./Dec. 2003, 329-336, vol. 20, No. 6, Health Communications Inc.
Newman, Nancy, Hereditary Optic Neuropathis: From The Mitochondria to The Optic Nerve, American Journal of Ophthalmology, 2005, 517e1-517e8, 140(3), US.
Noecker, Robert J., et al., Effect of Preservatives in Chronic Ocular Therapy, Clinical & Refractive Optometry, 2004, 43-48, 15:2.
Oculex, Oculex Announces Positive Clinical Results for Posurdex(r) the first biodegradable ocular implant, PR Newswire, Aug. 6, 2002, 1-2.
Olsen, Timothy et al, Human Scleral Permeability: Effects of Age, Cryotherapy, Transcleral Diode Laser, and Surgical Thinning, Invest. Ophthalmol. Vis. Sci., 1995, 1893-1903, 36.
Phillips, Calbert et al, Penetration of Timolol Eye Drops into Human Aqueous Humor: The First Hour, British Journal of Ophthalmology, 1985, 217-218, 69.
Phillips, Tania et al, Efficacy of 0.1% Tazarotene Cream for the treatment of Photodamage, Arch Dermatol, Nov. 2002, 1486-1493, 138(11).
Physician's Desk Reference for Ophthalmic Medicines, 30th Edition, 285-294, 2002.
Pribluda, Victor et al, 2-Methoxyestradiol: An Endogenous Antiangionic and Antiproliferative Drug Candidate, Cancer and Metastasis Reviews, 2000, 173-179, 19.
Quigley, Harry et al, The Mechanism of Optic Nerve Damage in Experimental Acute Intraocular Pressure Elevation, Invest. Ophthalmol. Vis. Sci., 1980, 505-517, 19.
Rao et al, Intraocular Inflammation and Uveitis, Basic and Clinical Science Course; Intraocular Inflammation and Uveitis, 1998-1999, 57-80; 102-103; 152-156, Section 9; Part 2.
Renfro, Lisa et al, Ocular Effects of Topical and Systemic Steroids, Dermatologic Clinics, 1992, 505-512, 10.
Roff, W.J. et al, Fibres, Films, Plastics and Rubbers, A Handbook of Common Polymers, 1971, 7 Pages, 1.
Rowe, Raymond et al, Aliphatic Polyesters, Handbook of Pharmaceutical Excipients, Nov. 19-21, 2003, 4th Edition.
Schmidt-Erfurth, Ursula et al, Management of Neovascular Age-Related Macular Degeneration, Progress in Retinal and Eye Research, 2007, 437-451, 26.
Schonfeld, David, Lumigan Found Effective in Early Phase 3, Ocul. Surg. News, Mar. 1, 2001, 35, 19(5)1.
Schuettauf, Frank et al, Effects of anti-glaucoma Medications on Ganglion Cell Survival: the DBA/2J Mouse Model, Vision Res., 2002, 2333-2337, 42(20).
Schumacher, Guido et al, The Physiological Estrogen Metabolite 2-Methoxyestradiol Reduced Tumor Growth and Induces Apoptosis in Human Solid Tumors, J Cancer Res Clin Oncol, 2001, 405-410, 127.
Schwartz, Bernard, The Response of Ocular Pressure to Corticosteroids, Ophthamol. Clin. North Am., 1966, 929-989, 6.
Siebold, Earlene et al, Esterified Prostaglandin Shows 'Potent' Promise, Ocular Surgery News, Feb. 1, 1989, pp. 3, 59, 1.
Skalka, Harold et al, Effect of Corticosteroids on Cataract Formation, Arch. Ophthalmol, 1980, 1773-1777, 98.
Smith, Thomas et al, Sustained-Release Subconjunctival 5-Fluorouracil, Ophthalmic Surgery and Laser, Sep. 1996, 763-767, 27-9.
Starr, Michael, Further Studies on the Effects of Prostagladin on Intraocular Pressure in the Rabbit, Exp. Eye Res., 1971, 170-177, 11.
Stewart, William et al, The Efficacy and Safety of Latanoprost 0.005% Once Daily Versus Brimonidine 0.2% Twice Daily in Open-Angle Glaucoma or Ocular Hypertension, Am J Ophthalmol, May 2001, 631-635, 131.
Tazarotene, Drugs Future, 208-209-2003.
Tracy, M.A. et al, Factors Affecting the Degradation Rate of Poly(actide-co-glycolide) Microspheres in Vivo and in Vitro, Biomaterials, 1999, 1057-1062, 20.
U.S. Appl. No. 10/837,143, filed Apr. 30, 2004.
U.S. Appl. No. 11/395,019, filed Mar. 31, 2006.
U.S. Appl. No. 10/836,911, filed Apr. 30, 2004.
United States Pharmacopeia, The National Formulary, USP23, 1995, 1790-1798, 18.
U.S. Appl. No. 11/119,021, filed Apr. 29, 2005.
U.S. Appl. No. 11/394,765, filed Mar. 31, 2006.
U.S. Appl. No. 11/927,613, filed Oct. 29, 2007.
U.S. Appl. No. 11/927,615, filed Oct. 29, 2007.
U.S. Appl. No. 12/024,010, filed Jan. 31, 2008.
U.S. Appl. No. 12/024,014, filed Jan. 31, 2008.
U.S. Appl. No. 12/142,071, filed Jun. 19, 2008.
U.S. Appl. No. 12/142,083, filed Jun. 19, 2008.
U.S. Appl. No. 13/154,079, filed Jun. 6, 2011.
U.S. Appl. No. 11/118,519, filed Apr. 29, 2004.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Wheeler, L.A. et al, Alpha-2adrenergic Receptor Agonists Are Neuroprotective in Experimental Models of Glaucoma, Eur J Ophthalmol, 2001, S30-S35, 11(Suppl 2).
Wheeler, Larry et al, Role of Alpha-2 Adrenergic Receptors in Neuroprotection and Glaucoma, Surv Ophthalmol, May 2001, S290-S294, vol. 45, Supplement 3.
Wheeler, Larry, Experimental Study of Agents with Potential Neuroprotective Properties, Acta Ophthalmol Scand, 1999, 27-28, 77.
Woldemussie, Elizabeth et al, Neuroprotection Effects of Memantine in Different Retinal Injury Models of Glaucoma, J Glaucoma, 2002, 474-480, 11(6).

(56) References Cited

OTHER PUBLICATIONS

Woldemussie, Elizabeth, Neuroprotection of Retinal Ganglion Cells in Experimental Models of Glaucoma, Minerva Ophthalmol, 2000, 71-78, 42(2).
Woodward, David et al, AGN 192024 (LumiganR): A Synthetic Prostamide Analog that Lowers Primate Intraocular Pressure by Virtue of Its Inherent Pharmacological Activity, ARVO, 2002, 1 page (Abstract), 43.
Woodward, David et al, Pharmacology of Bimatoprost (LumiganTM), Survey of Ophthalmology, May 2001, S337-S345, vol. 45.
Yasukawa, T. et al., Biodegradable Scleral Plugs for Vitreoretinal Drug Delivery, Advanced Drug Delivery Reviews, 2001, 25-36, 52, US.
Zhou, Tianhong et al, Development of a Multiple-Drug Delivery Implant for Intraocular Management of Proliferative Vitreoretinopathy, Journal of Controlled Release, 1998, 281-295, 55.

US 10,201,641 B2

SUSTAINED RELEASE INTRAOCULAR IMPLANTS AND METHODS FOR TREATING OCULAR VASCULOPATHIES

CROSS-REFERENCE TO RELATED APPLICATIONS

This application is a continuation of copending U.S. patent application Ser. No. 12/024,010, filed on Jan. 31, 2008, which is a divisional of U.S. patent application Ser. No. 10/836,911, filed on Apr. 30, 2004, now abandoned, the entire content of which are hereby incorporated by reference.

BACKGROUND

The present invention generally relates to devices and methods to treat an eye of a patient, and more specifically to intraocular implants that provide extended release of a therapeutic agent to an eye in which the implant is placed, and to methods of making and using such implants, for example, to treat ocular vasculopathies, or to generally improve vision.

Brimonidine, 5-bromo-6-(2-imidazolidinylideneamino) quinoxaline, is an alpha-2-selective adrenergic receptor agonist that is effective in the treatment of open-angle glaucoma by decreasing aqueous humor production and increasing uveoscleral outflow. Brimonidine is available in two chemical forms, brimonidine tartrate and brimonidine free base. Brimonidine tartrate (Alphagan® P) is publicly available by Allergan for treating glaucoma. Topical ocular brimonidine formulation, 0.15% Alphagan® P (Allergan, Irvine, Calif.), is currently commercially available for treatment of open-angle glaucoma. The solubility of brimonidine tartrate in water is 34 mg/mL, while the solubility of brimonidine freebase is negligible in water.

Recent studies have suggested that brimonidine can promote survival of injured retinal ganglion nerve cells by activation of the alpha-2-adrenoceptor in the retina and/or optic nerve. For example, brimonidine can protect injured neurons from further damage in several models of ischemia and glaucoma.

Glaucoma-induced ganglion cell degeneration is one of the leading causes of blindness. This indicates that brimonidine can be utilized in a new therapeutic approach to glaucoma management in which neuroprotection and intraocular pressure reduction are valued outcomes of the therapeutic regimen. For brimonidine to protect the optic nerve, however, it must have access to the posterior segment of the eye at therapeutic levels. Currently available techniques for administering brimonidine to the posterior chamber of the eye are not sufficient to address this issue.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements that may be placed in an eye. The present systems and methods advantageously provide for extended release times of one or more therapeutic agents. Thus, the patient in whose eye the implant has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about two and about six months after receiving an implant. Such extended release times facilitate obtaining successful treatment results.

Intraocular implants in accordance with the disclosure herein comprise a therapeutic component and a drug release sustaining component associated with the therapeutic component. In accordance with the present invention, the therapeutic component comprises, consists essentially of, or consists of, an alpha-2 adrenergic receptor agonist. The alpha-2 adrenergic receptor agonist may be an agonist or agent that selectively activates alpha-2 adrenergic receptors, for example by binding to an alpha-2 adrenergic receptor, relative to other types of adrenergic receptors, such as alpha-1 adrenergic receptors. The selective activation can be achieved under different conditions, but preferably, the selective activation is determined under physiological conditions, such as conditions associated with an eye of a human or animal patient. The drug release sustaining component is associated with the therapeutic component to sustain release of an amount of the alpha-2 adrenergic receptor agonist into an eye in which the implant is placed. The amount of the alpha-2 adrenergic receptor agonist is released into the eye for a period of time greater than about one week after the implant is placed in the eye and is effective in preventing or reducing ocular vasculopathies, such as vascular occlusions.

In one embodiment, the intraocular implants comprise an alpha-2 adrenergic receptor agonist and a biodegradable polymer matrix. The alpha-2 adrenergic receptor agonist is associated with a biodegradable polymer matrix that degrades at a rate effective to sustain release of an amount of the agonist from the implant for a time sufficient to reduce or prevent an ocular vascular occlusion. The intraocular implant is biodegradable or bioerodible and provides a sustained release of the alpha-2 adrenergic receptor agonist in an eye for extended periods of time, such as for more than one week, for example for about three months or more and up to about six months or more. In certain implants, the alpha-2 adrenergic receptor agonist is released for about 30-35 days or less. In other implants, the alpha-2 adrenergic receptor agonist is released for 40 days or more.

The biodegradable polymer component of the foregoing implants may be a mixture of biodegradable polymers, wherein at least one of the biodegradable polymers is a polylactic acid polymer having a molecular weight less than 64 kiloDaltons (kD). Additionally or alternatively, the foregoing implants may comprise a first biodegradable polymer of a polylactic acid, and a different second biodegradable polymer of a polylactic acid. Furthermore, the foregoing implants may comprise a mixture of different biodegradable polymers, each biodegradable polymer having an inherent viscosity in a range of about 0.3 deciliters/gram (dl/g) to about 1.0 dl/g.

The alpha-2 adrenergic receptor agonist of the implants disclosed herein may include quinoxaline derivatives, or other agonists that are effective in treating ocular conditions. One example of a suitable quinoxaline derivative is brimonidine or brimonidine tartrate. In addition, the therapeutic component of the present implants may include one or more additional and different therapeutic agents that may be effective in treating an ocular condition.

A method of making the present implants involves combining or mixing the alpha-2 adrenergic receptor agonist with a biodegradable polymer or polymers. The mixture may then be extruded or compressed to form a single composition. The single composition may then be processed to form individual implants suitable for placement in an eye of a patient.

The implants may be placed in an ocular region to treat a variety of ocular conditions, including conditions such as ocular vasculopathies that affect an anterior region or posterior region of an eye. For example, the implants may be used to treat many conditions of the eye, including, without limitation, conditions associated with vascular occlusion.

Kits in accordance with the present invention may comprise one or more of the present implants, and instructions for using the implants. For example, the instructions may explain how to administer the implants to a patient, and types of conditions that may be treated with the implants.

Each and every feature described herein, and each and every combination of two or more of such features, is included within the scope of the present invention provided that the features included in such a combination are not mutually inconsistent. In addition, any feature or combination of features may be specifically, excluded from any embodiment of the present invention.

Additional aspects and advantages of the present invention are set forth in the following description and claims, particularly when considered in conjunction with the accompanying drawings.

DRAWINGS

DESCRIPTION

Figure 1:
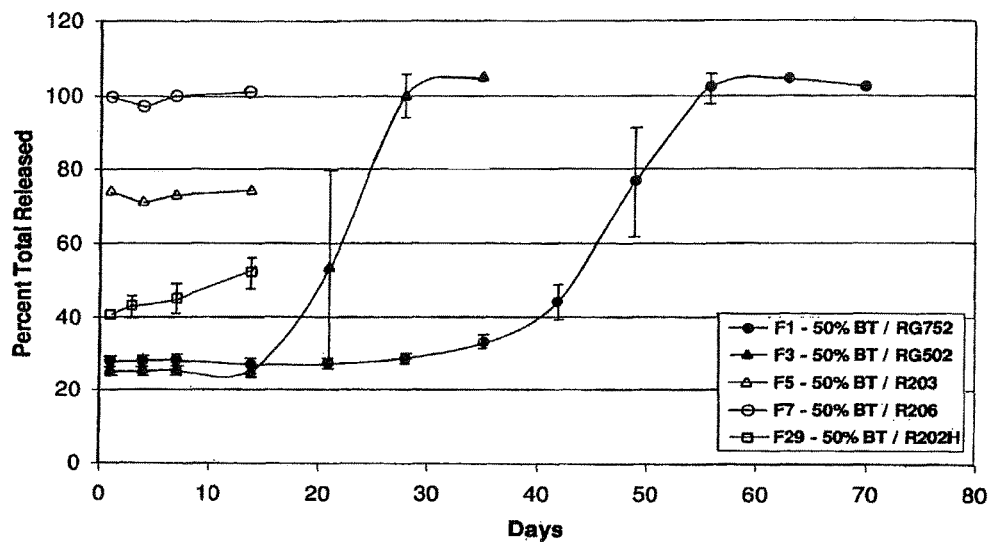
FIG. 1 is a graph showing the cumulative release profiles for biodegradable brimonidine tartrate containing implants as determined in 0.9% phosphate buffered saline at 37 degrees Celsius.

As described herein, controlled and sustained administration of a therapeutic agent through the use of one or more intraocular implants may improve treatment of undesirable ocular conditions. The implants comprise a pharmaceutically acceptable polymeric composition and are formulated to release one or more pharmaceutically active agents, such as alpha-2 adrenergic receptor agonists, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or, in the case of self-administered drops, ineffective treatment with only limited bursts of exposure to the active agent or agents.

An intraocular implant in accordance with the disclosure herein comprises a therapeutic component and a drug release sustaining component associated with the therapeutic component. In accordance with the present invention, the therapeutic component comprises, consists essentially of, or consists of, an alpha-2 adrenergic receptor agonist. The drug release sustaining component is associated with the therapeutic component to sustain release of a therapeutically effective amount of the alpha-2 adrenergic receptor agonist into an eye in which the implant is placed. The therapeutic amount of the alpha-2 adrenergic receptor agonist is released into the eye for a period of time greater than about one week after the implant is placed in the eye.

Definitions

For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time is occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

Intraocular implants have been developed which can release drug loads over various' time periods. These implants, which when inserted into an eye, such as the vitreous of an eye, provide therapeutic levels of an alpha-2 adrenergic receptor agonist for extended periods of time (e.g., for about 1 week or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises an alpha-2 adrenergic receptor agonist associated with the biodegradable polymer matrix. The matrix degrades at a rate effective to sustain release of an amount of the alpha-2 adrenergic receptor agonist for a time greater than about one week from the time in which the implant is placed in ocular region or ocular site, such as the vitreous of an eye.

The alpha-2 adrenergic receptor agonist of the implant is typically an agent that selectively activates alpha-2 adrenergic receptors relative to alpha-1 adrenergic receptors. In certain implants, the alpha-2 adrenergic receptor agonist is selectively activates a subtype of the alpha-2 adrenergic receptors. For example, the agonist may selectively activate one or more of the alpha-2a, the alpha-2b, or the alpha-2c receptors, under certain conditions, such as physiological conditions. Under other conditions, the agonist of the implant may not be selective for alpha-2 adrenergic receptor subtypes. The agonist may activate the receptors by binding to the receptors, or by any other mechanism.

In certain implants, the alpha-2 adrenergic receptor agonist is a quinoxaline derivative. The quinoxaline derivatives useful in the present implants are those quinoxaline derivatives having the formula,

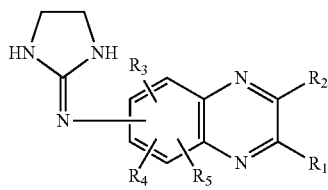

pharmaceutically acceptable acid addition salts thereof, and mixtures thereof. $R_1$ and $R_2$ each is independently selected from the group consisting of H, alkyl radicals containing 1 to 4 carbon atoms and alkoxy radicals containing 1 to 4 carbon atoms. $R_2$ is preferably a methyl radical. The 2-imidazolin-2-ylamino group may be in any of the 5-, 6-, 7- and 8-positions, preferably in the 6-position, of the quinoxaline nucleus. $R_3$, $R_4$ and $R_5$ each is located in one of the remaining 5-, 6-, 7- or 8-positions of the quinoxaline nucleus and is independently selected from the group consisting of Cl, Br, H and alkyl radicals containing 1 to 3 carbon atoms. $R_3$ is preferably in the 5-position of the quinoxaline nucleus, and $R_4$ and $R_5$ are preferably both H. In a particularly useful embodiment $R_3$ is Br.

In at least one implant, $R_1$ is H and $R_2$ is selected from alkyl radicals containing 1 to 4 carbon atoms. $R_3$ may advantageously be in the 5-position of the quinoxaline nucleus and be selected from H and alkyl radicals containing 1 to 3 carbon atoms. All stereoisomers, tautomers and mixtures thereof which comply with the constraints of one or more of the presently useful compounds are included within the scope of the present invention.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In more specific implants, the quinoxaline derivative has the formula

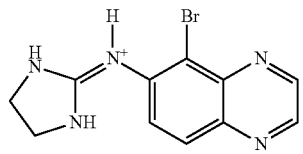 [SMILES: Brc1c([NH+]=C2NCCN2)ccc2nccnc12]

In additional implants, the alpha-2 adrenergic receptor agonist is provided as a salt having the formula

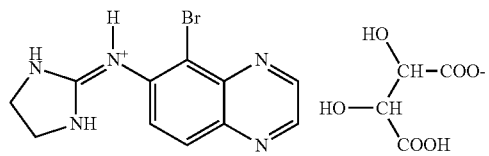

The foregoing salt is known as brimonidine tartrate (AGN 190342-F, 5-bromo-6-(2-imidazolidinylideneamino)quinoxaline tartrate), and is publicly available from Allergan, Inc. under the tradename Alphagan®-P. Brimonidine, an organic base, is publicly available as either brimonidine tartrate salt or as brimonidine freebase. The tartrate salt is more soluble than the freebase in various aqueous media. Since both the tartrate salt and the freebase are chemically stable and have melting points higher than 200° C., both forms are suitable in forming the present implants.

Thus, the implant may comprise a therapeutic component which comprises, consists essentially of, or consists of a brimonidine salt, such as brimonidine tartrate, a brimonidine free base, or mixtures thereof.

The alpha-2 adrenergic receptor agonist may be in a particulate or powder form and entrapped by the biodegradable polymer matrix. Usually, alpha-2 adrenergic receptor agonist particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The alpha-2 adrenergic receptor agonist of the implant is preferably from about 10% to 90% by weight of the implant. More preferably, the alpha-2 adrenergic receptor agonist is from about 20% to about 80% by weight of the implant. In a preferred embodiment, the alpha-2 adrenergic receptor agonist comprises about 20% by weight of the implant (e.g., 15%-25%). In another embodiment, the alpha-2 adrenergic receptor agonist comprises about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or combination of both. As discussed herein, the matrix of the intraocular implant may release drug at a rate effective to sustain release of an amount of the alpha-2 adrenergic receptor agonist for more than one week after implantation into an eye. In certain implants, therapeutic amounts of the alpha-2 adrenergic receptor agonist are released for no more than about 30-35 days after implantation. For example, an implant may comprise brimonidine tartrate, and the matrix of the implant degrades at a rate effective to sustain release of a therapeutically effective amount of brimonidine tartrate for about one month after being placed in an eye. As another example, the implant may comprise brimonidine tartrate, and the matrix releases drug at a rate effective to sustain release of a therapeutically effective amount of brimonidine tartrate for more than forty days, such as for about six months.

One example of the biodegradable intraocular implant comprises an alpha-2 adrenergic receptor agonist associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the alpha-2 adrenergic receptor agonist for a time period greater than about one month from the time the implant is placed in an eye.

Another example of a biodegradable intraocular implant comprises an alpha-2 adrenergic receptor agonist associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. The inherent viscosities identified above may be determined in 0.1% chloroform at 25° C.

One particular implant comprises brimonidine tartrate associated with a combination of two different polylactide polymers. The brimonidine tartrate is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant provides for release of the brimonidine for more than two months in vitro, as described herein. The implant is provided in the form of a rod or a filament produced by an extrusion process.

The release of the alpha-2 adrenergic receptor agonist from the intraocular implant comprising a biodegradable polymer matrix may include an initial burst of release followed by a gradual increase in the amount of the alpha-2 adrenergic receptor agonist released, or the release may include an initial delay in release of the alpha-2 adrenergic receptor agonist followed by an increase in release. When the implant is substantially completely degraded, the percent of the alpha-2 adrenergic receptor agonist that has been released is about one hundred. Compared to existing implants, the implants disclosed herein do not completely release, or release about 100% of the alpha-2 adrenergic receptor agonist, until after about one week of being placed in an eye.

It may be desirable to provide a relatively constant rate of release of the alpha-2 adrenergic receptor agonist from the implant over the life of the implant. For example, it may be desirable for the alpha-2 adrenergic receptor agonist to be released in amounts from about 0.01 µg to about 2 µg per day for the life of the implant. However, the release rate may change to either increase or decrease depending on the formulation of the biodegradable polymer matrix. In addition, the release profile of the alpha-2 adrenergic receptor agonist may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the alpha-2 adrenergic receptor agonist, may be distributed in a non-homogenous pattern in the matrix. For example, the implant may include a portion that has a greater concentration of the alpha-2 adrenergic receptor agonist relative to a second portion of the implant.

The intraocular implants disclosed herein may have a size of between about 5 µm and about 2 mm, or between about 10 µm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of alpha-2 adrenergic receptor agonist, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the alpha-2 adrenergic receptor agonist or alpha-2 adrenergic receptor agonists included in the intraocular implants disclosed herein, the intraocular implants may also include one or more additional ophthalmically acceptable therapeutic agents. For example, the implant may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, triamcinolone hexacetonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valaciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamylcysteine, quercetin, lactoferrin, dihydrolipoic acid, citrate, Ginkgo Biloba extract, tea catechins, bilberry extract, vitamins E or esters of vitamin E, retinyl palm itate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfate, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight. In at least one of the present implants, a purite preservative is provided in the implant, such as when the alpha-2 adrenergic receptor agonist is brimonidine. Thus, these implants may contain a therapeutically effective amount of Alphagan®-P.

In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the alpha-2 adrenergic receptor agonist in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant comprising brimonidine or brimonidine tartrate and a biodegradable polymer matrix is able to release or deliver an amount of brimonidine between about 0.1 mg to about 0.5 mg for about 3-6 months after implantation into the eye. The implant may be configured as a rod or a wafer. A rod-shaped implant may be derived from filaments extruded from a 720 μm nozzle and cut into 1 mg size. A wafer-shaped implant may be a circular disc having a diameter of about 2.5 mm, a thickness of about 0.127 mm, and a weight of about 1 mg.

The proposed 3-month release formulations may be sterile, and bioerodible in the form of a rod, a wafer or a microsphere containing brimonidine tartrate within a PLA matrix or POE matrix. The implants are designed to delay the clearance of the drug and reduce the need for repeated implantation over 3-month period, thereby lowering the risk of complications.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997, 652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release'rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The present implants are configured to release an amount of alpha-2 adrenergic receptor agonist in an eye for a period of time to minimize an ocular vascular occlusion, such as a retinal vascular occlusion. Retinal vascular occlusion may result from a variety of diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, hemi-retinal vein occlusion, central retinal artery occlusion, branch retinal artery occlusion, carotid artery disease (cad), eales disease and vasculopathies associated with diabetes. By implanting the alpha-2 adrenergic receptor agonist-containing implants into the vitreous of an eye, it is believed that the agonist is effective to reduce occlusion within blood vessels located in the eye.

In addition, the present implants may be configured to release an alpha-2 adrenergic receptor agonist in a therapeutically effective amount for a period of time effective to treat glaucoma of a patient.

The implants disclosed herein may also be configured to release additional therapeutic agents, as described above, which may be effective in treating diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch, Angiitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (PONS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Associated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In at least one embodiment, a method of reducing retinal vascular occlusion in a patient comprises administering one or more implants containing one or more alpha-2adrenergic receptor agonists, as disclosed herein to a patient by at least one of intravitreal injection, subconjunctival injection, sub-tenon injection, retrobulbar injection, and suprachoroidal injection. A syringe apparatus including an appropriately sized needle, for example, a 27 gauge needle or a 30 gauge needle, can be effectively used to inject the composition with the posterior segment of an eye of a human or animal. Repeat injections are often not necessary due to the extended release of the alpha-2 adrenergic receptor agonists from the implants.

In another aspect of the invention, kits for treating an ocular condition of the eye are provided, comprising: a) a container comprising an extended release implant comprising a therapeutic component including an alpha-2 adrenergic receptor agonist, such as brimonidine free base or brimonidine tartrate (e.g., Alphagan-P), and a drug release sustaining component; and b) instructions for use. Instructions may include steps of how to handle the implants, how to insert the implants into an ocular region, and what to expect from using the implants.

EXAMPLE 1

Manufacture and Testing of Implants Containing Brimonidine and a Biodegradable Polymer Matrix Biodegradable implants were made by combining brimonidine tartrate or brimonidine freebase with a biodegradable polymer composition in a stainless steel mortar. The combination was mixed via a Turbula shaker set at 96 RPM for 15 minutes. The powder blend was scraped off the wall of the mortar and then remixed for an additional 15 minutes. The mixed powder blend was heated to a semi-molten state at specified temperature for a total of 30 minutes, forming a polymer/drug melt.

Rods were manufactured by pelletizing the polymer/drug melt using a 9 gauge polytetrafluoroethylene (PTFE) tubing, loading the pellet into the barrel and extruding the material at the specified core extrusion temperature into filaments. The filaments were then cut into about 1 mg size implants or drug delivery systems. The rods had dimensions of about 2 mm long×0.72 mm diameter. The rod implants weighed between about 900 μg and 1100 μg.

Wafers were formed by flattening the polymer melt with a Carver press at a specified temperature and cutting the flattened material into wafers, each weighing about 1 mg. The wafers had a diameter of about 2.5 mm and a thickness of about 0.13 mm. The wafer implants weighed between about 900 μg and 1100 μg.

The in-vitro release testing was performed on each lot of implant (rod or wafer) in six replicates initially, and later in four replicates. Each implant was placed into a 24 mL screw cap vial with 10 mL of Phosphate Buffered Saline solution at 37° C. and 1 mL aliquots were removed and replaced with equal volume of fresh medium on day 1, 4, 7, 14, 28, and every two weeks thereafter.

The drug assays were performed by HPLC, which consists of a Waters 2690 Separation Module (or 2696), and a Waters 2996 Photodiode Array Detector. An Ultrasphere, C-18 (2), 5 μm; 4.6×150 mm column heated at 30 ° C. was used for separation and the detector was set at 264 nm. The mobile phase was (10:90) MeOH-buffered mobile phase with a flow rate of 1 mL/min and a total run time of 12 min per sample. The buffered mobile phase comprised of (68: 0.75:0.25:31) 13 mM 1-Heptane Sulfonic Acid, sodium salt-glacial acetic acid-triethylamine-Methanol. The release rates were determined by calculating the amount of drug being released in a given volume of medium over time in μg/day.

The polymers chosen for the implants are were obtained from Boehringer Ingelheim. The polymers were: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

A total of 53 formulations were prepared, 31 rods and 22 wafers. Of the rod formulations, 4 had release periods longer than 3 months and 3 had release periods longer than 6 months. Of the wafer formulations, 7 had release periods longer than 3 months and 4 had release periods longer than 4 months.

A list of the rod formulations is shown in Table 1, and a list of wafer formulations is shown in Table 2.

TABLE 1

Brimonidine Rod Formulations

| Formulation | Lot | BT (w/w) | BFB (w/w) | Polymer | I.V. (dL/g) | Core Extr T |
|---|---|---|---|---|---|---|
| 1 | 295-123 | 50% | | RG752 | 0.2 | 104° C. |
| 2 | 295-124 | | 50% | RG752 | 0.2 | 105° C. |
| 3 | 295-126 | 50% | | RG502 | 0.2 | 108° C. |
| 4 | 295-127 | | 50% | RG502 | 0.2 | 112° C. |

TABLE 1-continued

Brimonidine Rod Formulations

| Formulation | Lot | BT (w/w) | BFB (w/w) | Polymer | I.V. (dL/g) | Core Extr T |
|---|---|---|---|---|---|---|
| 5 | 295-167 | 50% | | R203 | 0.3 | 98° C. |
| 6 | 295-168 | | 50% | R203 | 0.3 | 101° C. |
| 7 | 295-169 | 50% | | R206 | 1.0 | 118° C. |
| 8 | 295-170 | | 50% | R206 | 1.0 | 104° C. |
| 9 | 295-171 | 25% | | R206 | 1.0 | 98° C. |
| 10 | 295-172 | 25% | | R203 | 0.3 | 96° C. |
| 11 | 453-3 | 10% | 40% | R203 | 0.3 | 98° C. |
| 12 | 453-4 | 5% | 20% | R203 | 0.3 | 96° C. |
| 13 | 453-6 | 10% | 40% | R206 | 1.0 | 105° C. |
| 14 | 453-7 | 5% | 20% | R206 | 1.0 | 104° C. |
| 15 | 453-8 | 5% | 45% | R206 | 1.0 | 102° C. |
| 16 | 453-9 | 15% | | R206 | 1.0 | 102° C. |
| 17 | 453-10 | 20% | | (1:1) R203/R206 | N/A | 98° C. |
| 18 | 453-11 | 20% | | (3:1) R203/R206 | N/A | 96° C. |
| 19 | 453-12 | 10% | 40% | RG752 | 0.2 | 108° C. |
| 20 | 453-13 | 5% | 20% | RG752 | 0.2 | 104° C. |
| 24 | 453-50 | 20% | | R206 | 1.0 | 100° C. |
| 25 | 453-51 | 17% | | (1:1) R203/R206 | N/A | 98° C. |
| 26 | 453-52 | | 40% | (1:1) RG752/RG502 | N/A | 105° C. |
| 27 | 453-53 | | 40% | (3:1) RG752/RG502 | N/A | 103° C. |
| 28 | 453-54 | | 40% | (1:1) R203/RG502 | N/A | 103° C. |
| 29 | 453-55 | 50% | | R202H | 0.2 | 96° C. |
| 30 | 453-56 | | 50% | R202H | 0.2 | 98° C. |
| 31 | 453-73 | 20% | | RG752 | 0.2 | 98° C. |
| 32 | 453-74 | 20% | | Purac (Mw 9700) | N/A | 95° C. |
| 33 | 453-75 | | 20% | Purac (Mw 9700) | N/A | 92° C. |
| 53 | 453-95 | 20% | | (2:1) R203/R206 | N/A | 97° C. |

BT = Brimonidine Tartrate
BFB = Brimonidine Free Base
I.V. = Inherent Viscosity

TABLE 2

Brimonidine wafer Formulations

| Formulation | Lot | BT (w/w) | BFB (w/w) | Polymer | I.V. (dL/g) |
|---|---|---|---|---|---|
| 21 | 453-47 | 25% | | R206 | 1.0 |
| 22 | 453-48 | 20% | | (1:1) R203/R206 | N/A |
| 23 | 453-49 | 20% | | (3:1) R203/R206 | N/A |
| 34 | 453-76 | | 20% | (1:1) R203/R206 | N/A |
| 35 | 453-77 | | 25% | R206 | 1.0 |
| 36 | 453-78 | | 20% | (3:1) R203/R206 | N/A |
| 37 | 453-79 | | 25% | R203 | 0.3 |
| 38 | 453-80 | | 50% | R203 | 0.3 |
| 39 | 453-81 | | 50% | R206 | 1.0 |
| 40 | 453-82 | 15% | | R206 | 1.0 |
| 41 | 453-83 | | 40% | (1:1) RG752/RG502 | N/A |
| 42 | 453-84 | | 40% | (2:1) RG752/RG502 | N/A |
| 43 | 453-85 | | 40% | (1:1) R203/RG502 | N/A |
| 44 | 453-86 | | 50% | R202H | 0.2 |
| 45 | 453-87 | | 50% | (1:1) RG752/RG502 | N/A |
| 46 | 453-88 | 10% | | (1:1) R203/R206 | N/A |
| 47 | 453-89 | 15% | | (1:1) R203/R206 | N/A |
| 48 | 453-90 | 10% | | (3:1) R203/R206 | N/A |
| 49 | 453-91 | 15% | | (3:1) R203/R206 | N/A |
| 50 | 453-92 | 10% | | R206 | 1.0 |
| 51 | 453-93 | 10% | | (2:1) R203/R206 | N/A |
| 52 | 453-94 | 15% | | (2:1) R203/R206 | N/A |

BT = Brimonidine Tartrate
BFB = Brimonidine Free Base
I.V. = Inherent Viscosity

Rod Formulations

Figure 2:
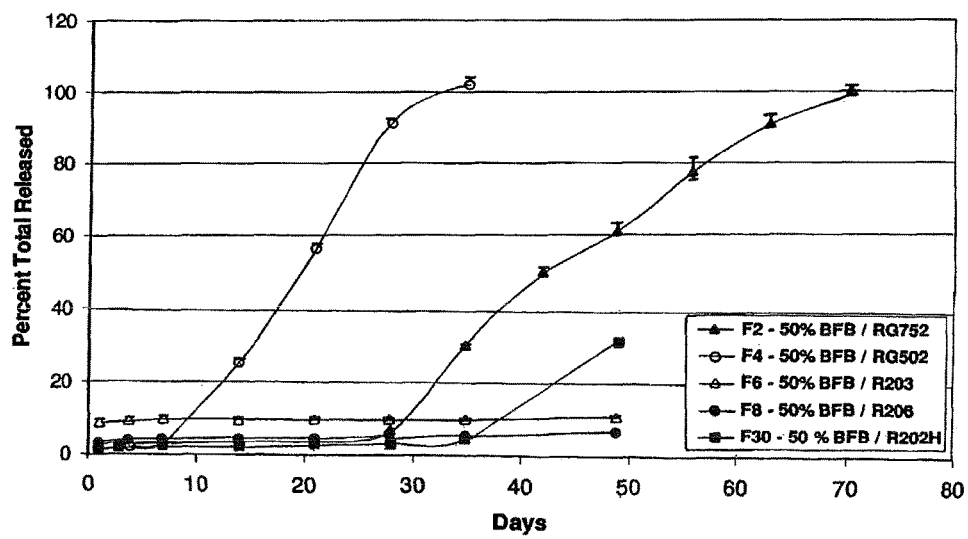
FIG. 2 is a graph similar to FIG. 1 showing the cumulative release profiles for biodegradable brimonidine free base containing implants with different combinations of biodegradable polymers.

The first 10 formulations were prepared with the five different polymers, RG752, RG502, R203, R206, and R202H each at 50% w/w drug load for both brimonidine tartrate and brimonidine free base. The release profiles are shown in FIG. 1 for brimonidine tartrate and FIG. 2 for brimonidine free base.

In most cases, formulations prepared with brimonidine tartrate had a faster initial burst than those prepared from brimonidine freebase using the same polymer, except for RG502. The data also show that brimonidine freebase had a lag time of approximately 30 days when formulated in poly(D, L-lactide) matrix (R203, R206, and R202H), while brimonidine tartrate was released completely on the first day (F5 and F7). This may be due to the quick dissolution of brimonidine tartrate on the surface of the implant.

Figure 3:
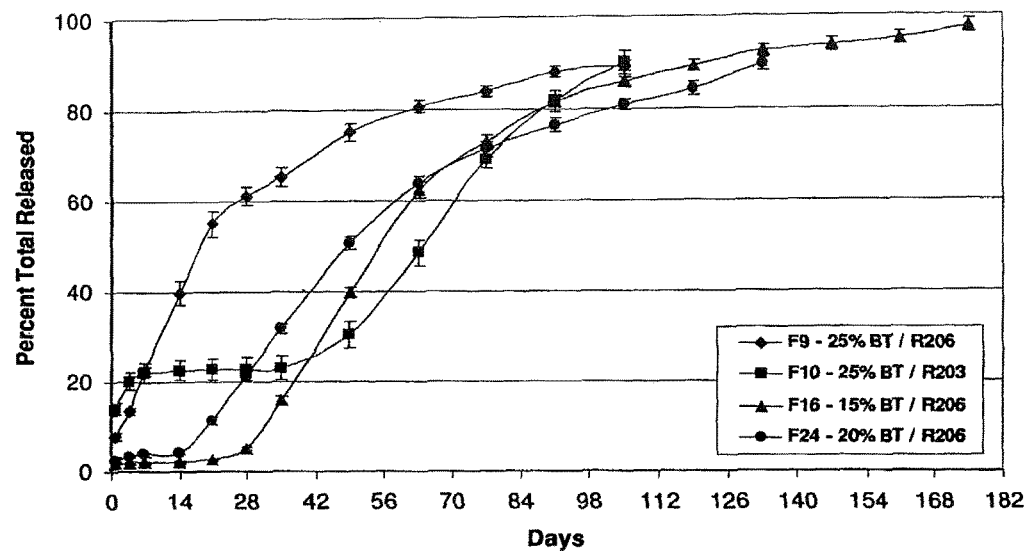
FIG. 3 is a graph similar to FIG. 1 showing the cumulative release profiles for biodegradable brimonidine tartrate containing implants having different concentrations of brimonidine tartrate.

Several formulations using R203 and R206 with drug doses lower than 50% were prepared, and the release profiles are shown in FIG. 3. Dramatic effects were observed when the drug load was lowered from 50% down to 25%. For example, formulation #9 was prepared with 25% brimonidine tartrate in R206 and it gave a total release of 89% after 105 days before leveling off. Comparing this to formulation #7, which was 50% brimonidine tartrate in R206, and it released 100% in one day. Similarly, formulation #10 was prepared with 25% brimonidine tartrate in R203 and it gave a total release of 90% after 105 days before it leveled off. Comparing this to formulation #5, which released 74% on day one.

With 20% brimonidine tartrate in R206 (F24), a 14 day lag time is present before it started releasing and eventually reaching 89.5% release after 134 days. At 15% brimonidine tartrate in R206 (F16), the lag time increased to 28 days before it started releasing and eventually reaching 97.6% after 175 days.

Figure 4:
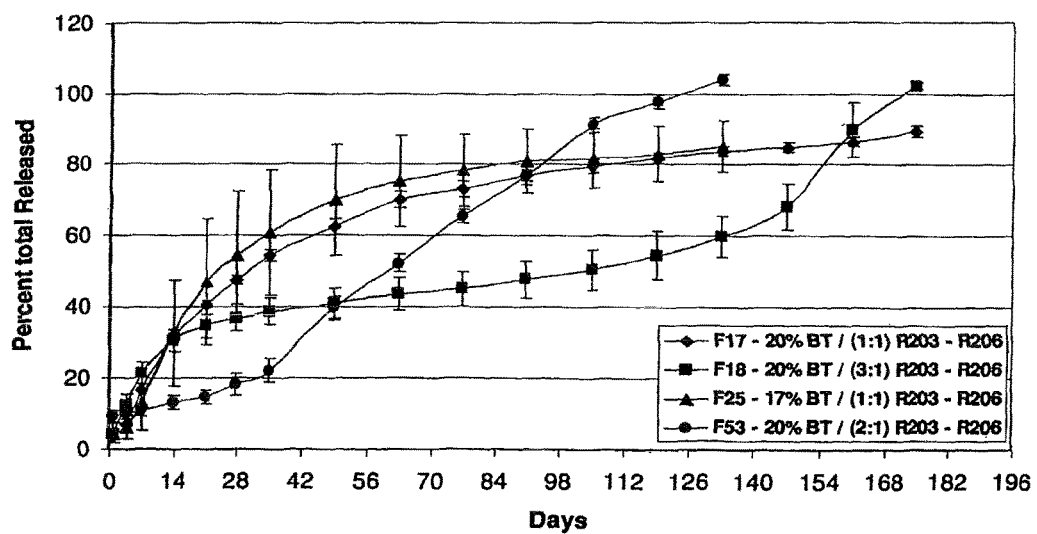
FIG. 4 is a graph similar to FIG. 3 showing the cumulative release profiles for biodegradable brimonidine tartrate containing implants having different concentrations of brimonidine tartrate and polymeric blends.

The release profiles of formulation #9 and #10 behaved in an opposite but complementary way, in that one polymer exhibits early release while the other exhibits a delayed release, but both reached the same end point at the same time When both polymers were combined with a lower drug load, a more linear and longer release profile would be obtained, as shown in FIG. 4.

The data show that formulation #17, 20% brimonidine tartrate/(1:1) R203/R206, has a desirable in-vitro release profile for a six month release implant. It released approximately 90% of the brimonidine tartrate after 175 days. It was also shown that by varying the proportion of R203 and R206, even with the same drug load (Formulation #17, #18, and #53), different release profiles would result.

Figure 5:
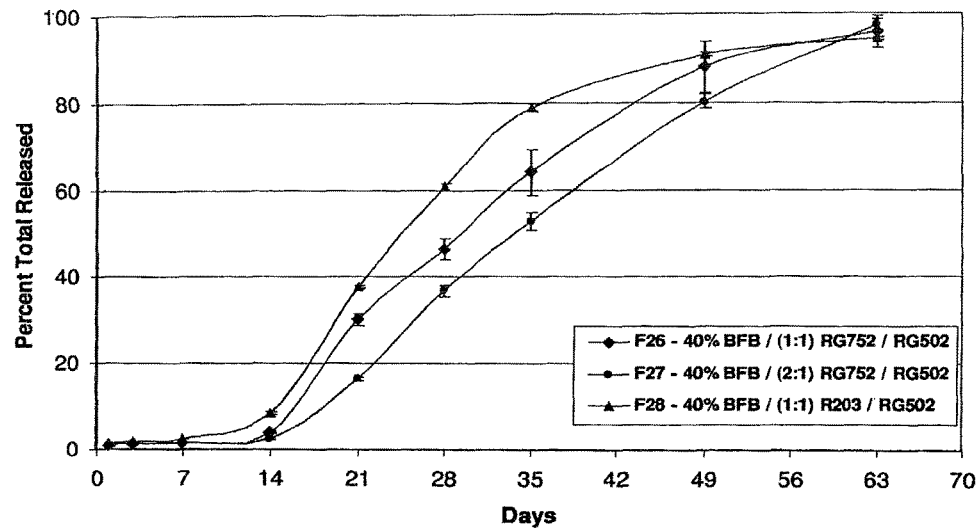
FIG. 5 is a graph similar to FIG. 4 showing the cumulative release profiles for biodegradable brimonidine free base containing implants having different concentrations of brimonidine tartrate and polymeric blends.

Brimonidine freebase formulations with polymer blends were also prepared to see if a more linear release profile could be obtained. Knowing its low solubility in aqueous media and its release characteristics in each polymer, different combinations of RG502-RG752, and RG502-R203 were prepared, and the release profiles are shown in FIG. 5.

The duration of release for all three formulations was approximately 2 months, but all three exhibited a lag time between 1 to 2 weeks. Two formulations (F32 and F33) were prepared with Purac polymer, PDLG (50/50)-Mw 9700, one with brimonidine tartrate and the one with brimonidine freebase. Both formulations had fast release with high standard of deviation; therefore, the release tests were stopped after 7 days.

Wafer Formulations

Figure 6:
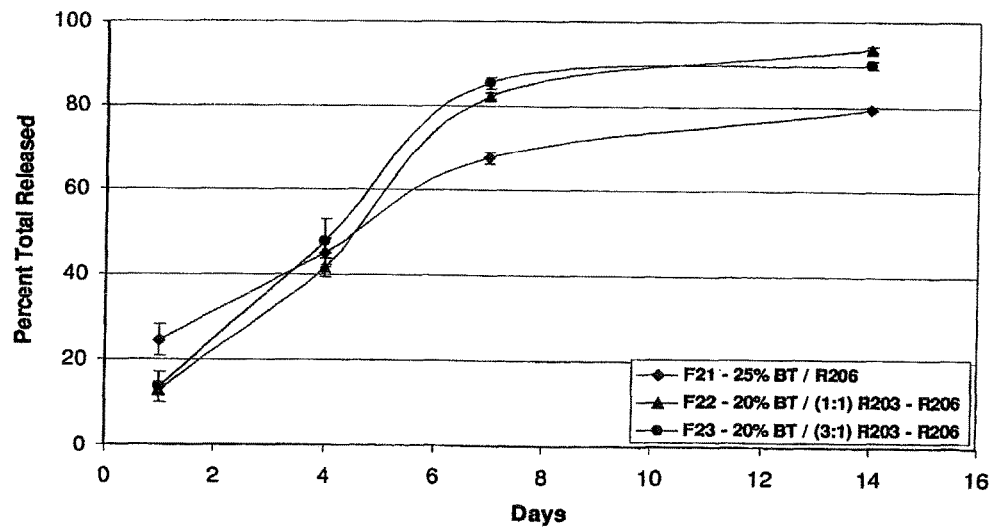
FIG. 6 is a graph showing the cumulative release profiles for brimonidine tartrate containing implants (wafers) having different concentrations of brimonidine tartrate and polymeric combinations.

The first set of wafer formulations was prepared from 3 existing rod formulations. Specifically, formulations #9, #17 and #18, with release reaching 89.4% after 105 days, 89.2% after 175 days, and 102% after 175 days, respectively. The release profiles of the first three wafer formulations are shown in FIG. 6.

Figure 7:
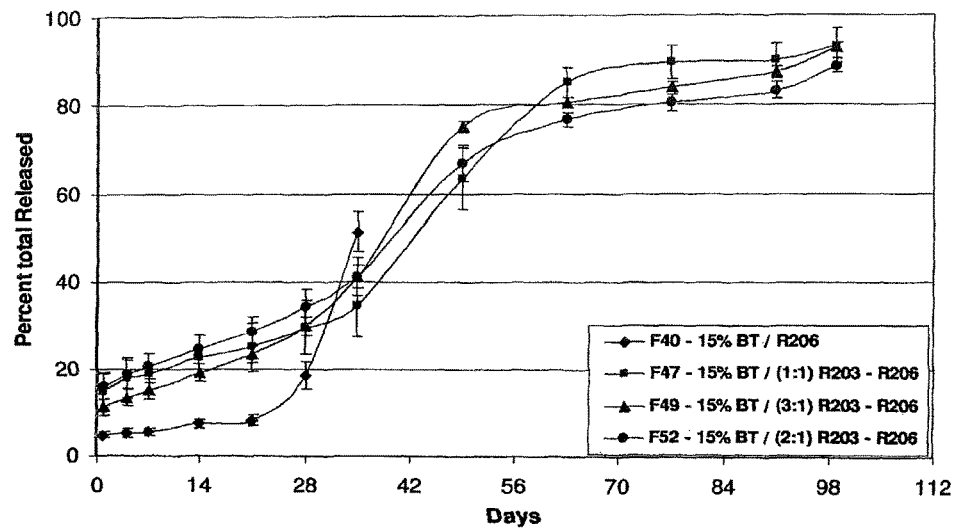
FIG. 7 is a graph similar to FIG. 6 showing the cumulative release profiles for biodegradable brimonidine free base containing implants having a different concentration of brimonidine tartrate and polymeric blends.
Figure 8:
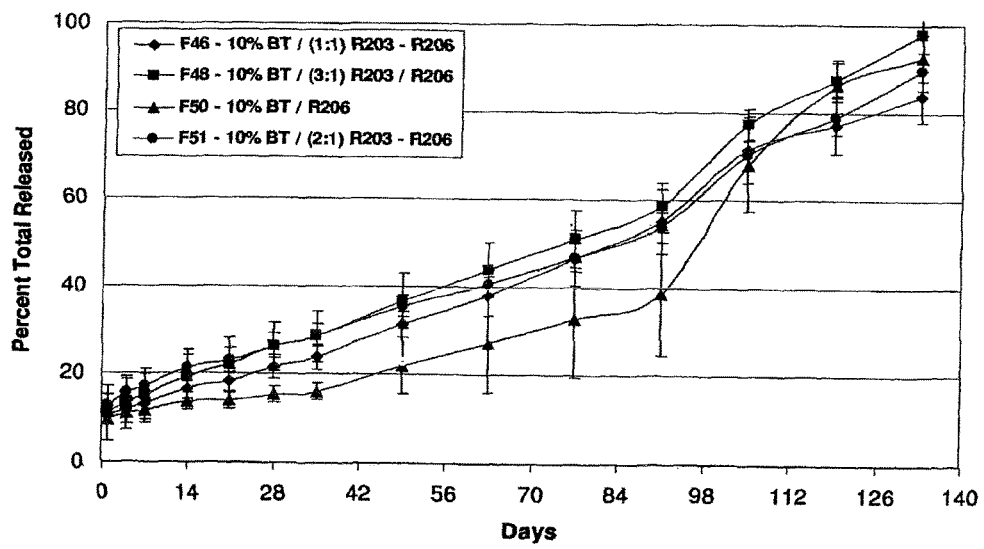
FIG. 8 is a graph similar to FIG. 4 showing the cumulative release profiles for biodegradable brimonidine free base containing implants having a different concentration of brimonidine tartrate and polymeric blends.

These three formulations had release periods lasting only two to three weeks, while their rod counterparts had release periods lasting three to four months. This may be due to the increased surface area of the wafer compared to that of a rod. In the wafer configuration, drug load also determines the duration of drug release. Therefore, drug load was reduced from 20-25% down to 15% and 10% and the release profiles are shown in FIGS. 7 and 8.

At 15% drug load, formulation #7 had a cumulative release 51.4% after 35 days, while formulation #47, 49, and 52 had cumulative releases of 93.2%, 92.8% and 88.5%, respectively, after 99 days. The latter three formulations may be effective as a 4-month drug delivery system.

At 10% drug load, formulations #46, #48, #50, and #51 had cumulative releases of 83.8%, 98.0%, 92.7% and 89.2%, respectively, after 133 days. These four formulations may be effective as 5-month drug delivery systems. Both FIGS. 7 and 8 demonstrate that lowering the drug load yielded not only a longer duration of release but also more linear release profiles for all formulations. The figures also show that using a polymer blend instead of just a single polymer, such as 8206, should yield a more linear release profile with lower standard of deviations.

Figure 9:
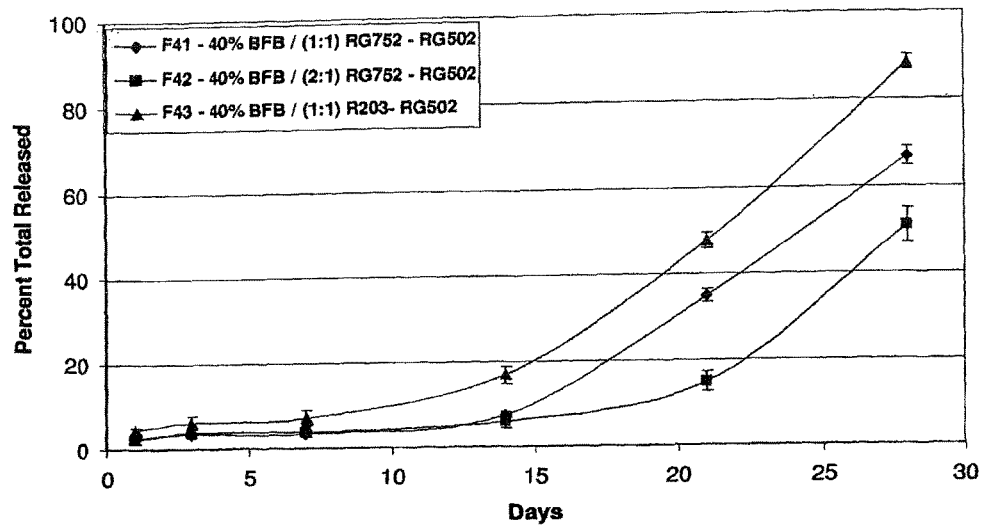
FIG. 9 is a graph similar to FIG. 5 showing the cumulative release profiles for biodegradable brimonidine free base containing wafer implants.

Three wafer formulations were prepared from three previous rod formulations #26, #27, and #28, and the release profiles are shown in FIG. 9. The three wafer formulations released slightly faster than their rod counterparts at day 28 and they were expected to complete their release between days 31 to 55.

CONCLUSIONS

Of the 15 rod formulations prepared from brimonidine tartrate, three formulations had release periods longer than 3 months (F9, F10, and F53), two formulations had release periods longer than 4 months (F24 and F25), and three formulations had release periods close to 6 months (F16, F17, and F18). Of the 8 rod formulations prepared from brimonidine freebase, 3 had release periods longer than 2 months (F26, F27, and F28).

Of the 22 wafer formulations, 11 were prepared from brimonidine tartrate and 11 were prepared from brimonidine freebase. Of the 11 wafer formulations prepared from brimonidine tartrate, 3 had release periods of about 4 months (F47, F49, and F52), and 4 had release periods between 4 and 5 months (F46, F48, F50, and F51). Of the 11 wafer formulations prepared from brimonidine freebase, 4 had release periods between 3 and 4 months (F35, F36, F38, and F39), and 5 had release periods between one to two months (F34, F37, F41, F42, and F43).

In general, the wafer formulations prepared from brimonidine tartrate or brimonidine freebase have faster release than their rod counterparts.

EXAMPLE 2

In Vivo Testing of Intraocular Implants Containing Brimonidine and a Biodegradable Polymer Matrix Cynomolgus monkeys were randomly assigned to receive either placebo (n=2) or brimonidine (n=2) formulated intravitreal implants. Baseline measures were performed 3 days prior to implantation and 10 days following implantation with intraocular pressure (1OP), mfERG, laser Doppler scanning topography/flowmetry (HRT/HRF), optical coherence tomography (OCT), indocyanine green angiography (ICG) and fluorescein angiography (FA).

Three implants (Formulation #17 described in Example 1), each formulated with 200 μg brimonidine or placebo were implanted intravitreally into an eye through a port made with an MVR blade (OS), the port was closed with sutures. Wide angle contact lens fundus photography verified implant count and localization.

Branch retinal vein occlusion (BRVO) was achieved by injecting 1 ml of 20 mg/kg Rose Bengal intravenously followed by thermal irradiation using Omni Coherent Diode laser at 532 nm, 600 mW, 50 um spot size, 0.01 sec pulse mode with a 1.6× inversion contact lens. Laser pulses were delivered until the vein segment was closed. One brimonidine treated monkey received 235 pulses and the other received 78 pulses. One placebo treated monkey received 43 pulses and the other received 31 pulses. Vascular occlusion of a vein was induced in the superior arcade approximately one disc diameter from the optic nerve head. Occlusion was verified post-laser by fundus photography.

Funduscopic observations at day 1 following BRVO showed dramatic retinopathy and vasculopathy in both monkeys with placebo implant—marked retinal edema and dot blot hemorrhages, vessel tortuosity, cotton wool spots. Fluorescein angiography verified vein occlusion and stagnate blood flow upstream from the lasered region and elucidated late phase fluorescein leak and pooling from retina capillaries. Monkeys with brimonidine implants had less than 5 small dot blot hemorrhages, some retinal edema localized to the superior retina. Fluorescein angiography in brimonidine monkeys showed reperfusion of the once occluded vein with minimal stagnate blood flow.

Figure 10:
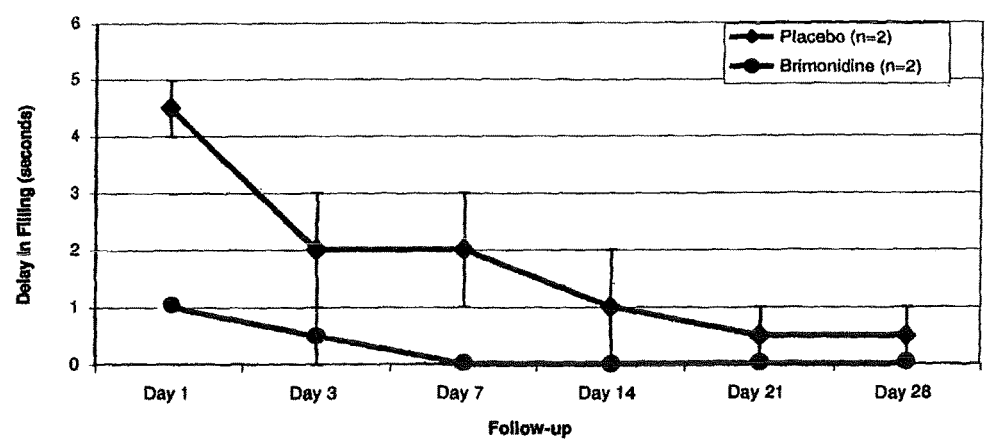
FIG. 10 is a graph showing the delay in filling of sodium fluorescein during angiography following branch retinal vein occlusion (BRVO) versus time in monkeys that have received brimonidine tartrate containing biodegradable implants or placebo implants.

The brimonidine containing implants decreased the duration of vascular occlusion as shown in FIG. 10. Delay in fluorescein filling of the occluded vein was quantified using Metamorph 6.0 software. Intensity measurements were made with pre-defined regions of interest for early and late phases of fluorescein angiography to quantify delay in filling and the observed delay in fluorescein clearance. The delay in early phase filling of fluorescein (seconds) in the occluded vein from baseline fluorescein angiography filling is illustrated in FIG. 10.

Figure 11:
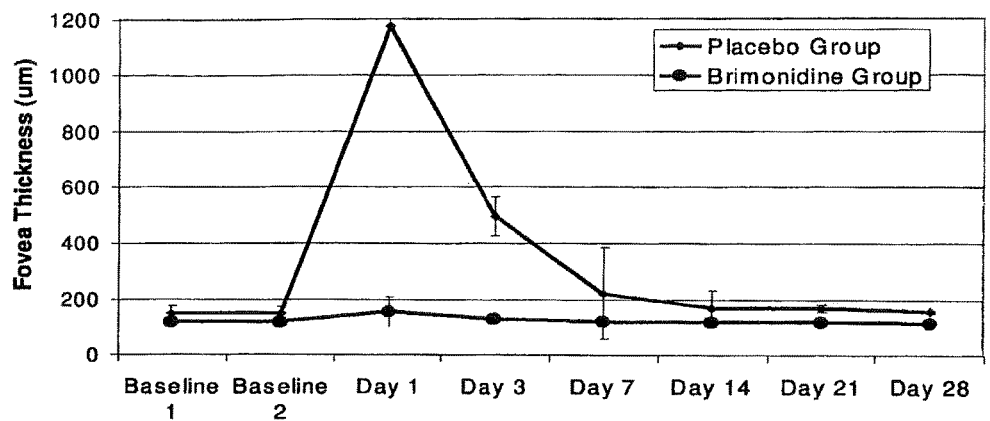
FIG. 11 is a graph of foveal thickness as a function of time in monkeys that have received brimonidine tartrate containing biodegradable implants or placebo implants and experienced BRVO.

Fovea thickness measurements from OCT single line scans (6 mm) show an increase in retinal edema as a result of vascular occlusion in the placebo group. Brimonidine containing implants decreased the magnitude of retinal edema associated with vascular occlusion. A series of line scans (covering 3 mm$^2$) directly compare changes in retinal thickness in the superior region surrounding the occluded vein with thickness changes in the inferior retina. Retinal edema in placebo monkeys was so profound that fluid accumulation occurred in the inferior region of the retina. In contrast, the brimonidine group did not have a significant change in inferior retina edema compared to baseline, as shown in FIG. 11.

Figure 12:
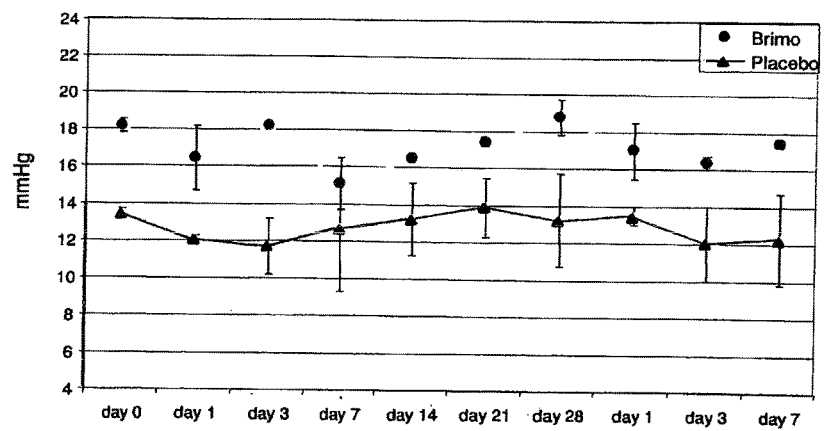
FIG. 12 is a graph of intraocular pressure as a function of time in monkeys that have received brimonidine tartrate containing biodegradable implants or placebo implants and experienced BRVO.

Intraocular pressure (IOP) was recorded (OD and OS) in each group in triplicate post implantation and prior to all follow-up electrophysiology and retinal imaging procedures. The brimonidine implants did not significantly lower IOP in eyes prior to or during BRVO, as shown in FIG. 12.

Figure 13:
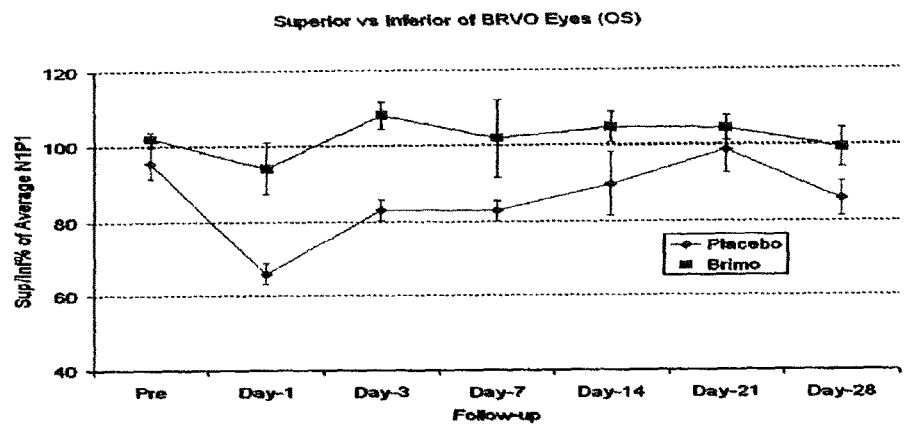
FIG. 13 is a graph of the superior/inferior percent response to a multifocal ERG as a function of time in monkeys that have received brimonidine tartrate containing biodegradable implants or placebo implants and experienced BRVO.

Multi-focal ERG was performed using a VERIS 5.0 system. A stimulus field of 241 hexagons was positioned to record superior retina and central retina foveal response. In the placebo group, foveal responses were absent through 3-4 weeks post BRVO induction, whereas, the foveal response in the brimonidine group was slightly lower but pronounced at day 1 following BRVO, with recovery and/or higher foveal response for the remainder of the study. The graph in FIG. 13 shows the superior/inferior % response for both groups. BRVO in monkeys treated with placebo have less responsive retinal function with a trend toward recovery late in the study versus relatively consistent retinal function with brimonidine implants.

Figure 14:
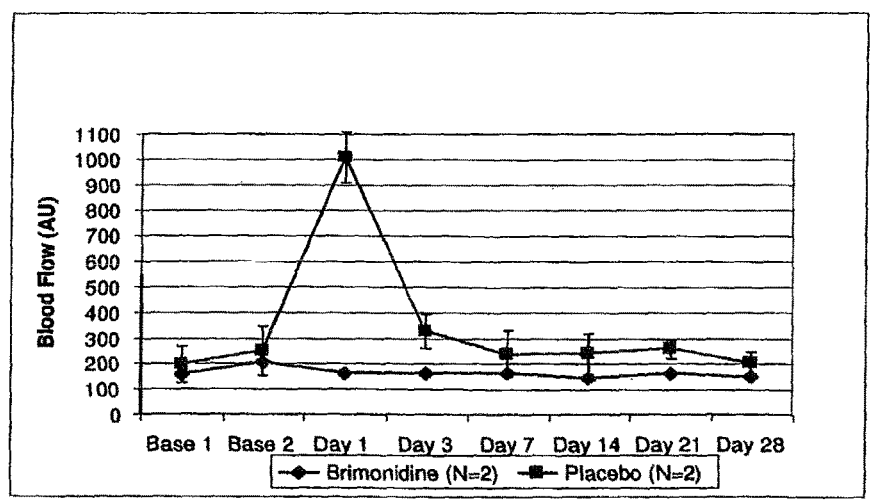
FIG. 14 is a graph of blood flow as a function of time in monkeys that have received brimonidine tartrate containing biodegradable implants or placebo implants and experienced BRVO.

Laser Doppler Flowmetry (HRF) was used to measure blood flow in the fovea, superior and inferior retina regions. The graph of FIG. 14 shows the results from blood flow measurements acquired with a 10-20 degree zone, centered at the fovea. Blood flow in the fovea appears to be unchanged in the brimonidine group following BRVO, but is sharply elevated at day 1 post BRVO in the placebo group.

Intravitreal application of three brimonidine intraocular implants has lessened the magnitude and duration of localized vascular occlusion and associated vasculopathy and retinopathy in monkeys.

In addition, the amount of laser burns needed to close the veins was higher in the brimonidine group compared to placebo (brimonidine: 157±79, n=2; placebo: 37±6, n=2). Together, these data show that the presence of brimonidine increases the difficulty of occluding retinal vasculature and decreases the duration of that occlusion.

EXAMPLE 3

Treatment of Glaucoma with an Intraocular Implant Containing Brimonidine Associated with a Biodegradable Polymer Matrix A 68 year old female complains to her physician that it is becoming difficult to see. The physician determines that she has elevated intraocular pressure levels, and diagnoses her with glaucoma. An implant containing 200 µg of brimonidine tartrate and 800 µg of a combination of biodegradable polymers (R203 and R206 at a 1:1 ratio, as described above in Example 1) is placed in the vitreous of both of the woman's eyes using a trocar. After about 2 days, the woman begins to notice a change in her eyes, presumably due to a decrease in intraocular pressure. The loss of vision is prevented for about five months after the implant procedure.

EXAMPLE 4

Treatment of Ocular Conditions with Various Active Agents

An implant can be formulated with various active agents, including the agents described herein, following the procedures in the Examples above. These implants can provide an extended therapeutic treatment of an ocular condition, that is a therapeutic effect during a period of time during release of the active agent or after release of all of the active agent from the implant and during which there is no longer a therapeutic amount of the active agent present at the ocular site at which the implant was placed. Thus, an implant can be prepared containing an alpha-2 adrenergic receptor agonist, such as clonidine, apraclonidine, or brimonidine (available from Allergan, Irvine, Calif. as brimonidine tartrate ophthalmic solution, under the tradename Alphagan®-P). Thus, for example, a brimonidine extended therapeutic treatment implant can be implanted into an ocular site (i.e. into the vitreous) of a patient with an ocular condition for a desired extended therapeutic effect. The implant may contain from about 50 µg to about 500 µg of Alphagan or Alphagan-P depending on the size of the implant. The brimonidine extended therapeutic treatment implant can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using the procedure such as trocar implantation. The implant can release a therapeutic amount of the active agent to provide and retain a therapeutic effect for an extended period of time to thereby treat a symptom of an ocular condition. For example, the implant may be effective to improve visual acuity, visual contract sensitivity, or both.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A method of treating macular degeneration in an eye of a patient, comprising the step of placing a solid extruded biodegradable intraocular implant in an eye of the patient to provide a therapeutically effective amount of brimonidine freebase to the patient for at least about one week, wherein said implant comprises brimonidine freebase associated with a biodegradable polymer matrix that releases drug at a rate effective to sustain release of an amount of the brimonidine freebase from the implant for a time effective to treat macular degeneration in an eye in which the implant is placed, the time being at least about one week after the implant is placed in the eye and wherein said polymer matrix comprises two different polylactide polymers in a 1:1 ratio wherein said first polylactide polymer has a molecular weight of 63.3 kD and said second polylactide polymer has a molecular weight of about 14 kD.

2. The method of claim 1, wherein the macular degeneration is selected from the group consisting of acute macular degeneration, non-exudative age related macular degeneration and exudative age related macular degeneration.

3. The method of claim 1, wherein the implant is placed in the posterior of the eye.

4. The method of claim 1, wherein the implant is placed in the eye with a trocar.

5. The method of claim 1, wherein the implant is placed in the eye with a syringe.

6. The method of claim 1, further comprising a step of administering a therapeutic agent in addition to the brimonidine freebase to the patient.

\* \* \* \* \*